(12) United States Patent
Kogan et al.

(10) Patent No.: US 6,673,226 B1
(45) Date of Patent: Jan. 6, 2004

(54) VOLTAMMETRIC MEASUREMENT OF HALIDE ION CONCENTRATION

(75) Inventors: Alex Kogan, Carlstadt, NJ (US); Eugene Shalyt, Washington Township, NJ (US); Peter Bratin, Flushing, NY (US); Michael Pavlov, Fairlawn, NJ (US); Michael James Perpich, Hackensack, NJ (US)

(73) Assignee: ECI Technology, East Rutherford, NJ (US)

(*) Notice: Subject to any disclaimer, the term of this patent is extended or adjusted under 35 U.S.C. 154(b) by 0 days.

(21) Appl. No.: 10/325,334

(22) Filed: Dec. 20, 2002

(51) Int. Cl.⁷ .................. G01N 27/26; C25D 21/12
(52) U.S. Cl. .............. 205/81; 205/101; 205/778.5; 205/789; 436/101; 436/125
(58) Field of Search ............... 205/81, 101, 778.5, 205/789; 436/101, 125

(56) References Cited

U.S. PATENT DOCUMENTS 6,572,753 B2 * 6/2003 Chalyt et al. ............... 205/81

OTHER PUBLICATIONS

Hill and Rogers, J. Electroanal. Chem. 86, p. 179–188 (1978), (no month given).
Yokoi, Konishi and Hayashi, Denki Kagaku 52(4), p. 218–223 (1984), (no month given).
Reid and David, Plating Surf. Fin. 74(1), p. 66–70 (1987), (no month given).
Kelly and West, J. Electrochem. Soc. 145(10), p. 3472–3476 (1998), (no month given).
Kelly, Tian and West, J. Electrochem. Soc. 146(7), p. 2540–2545 (1999), (no month given).
Mikkola and Chen, Proc. IEEE 2000 Int. Interconnect Tech. Conf., p. 117–120 (2000). (Jun. 2000).

* cited by examiner

Primary Examiner—Robert R. Koehler
(74) Attorney, Agent, or Firm—D. Morgan Tench

(57) ABSTRACT

The concentration of chloride ion in an acid copper electroplating bath is determined from the effect that chloride exerts on the copper electrodeposition rate in the presence of organic additives. A cyclic voltammetric stripping (CVS) rate parameter is measured, before and after standard addition of a plating bath sample, in an acid copper electrodeposition solution containing little or no chloride and at least one organic additive. Cross contamination and waste disposal issues associated with the reagents and reaction products involved in chloride titration analyses are avoided. The method may also be applied to analysis of other halides (bromide and iodide) and other solutions.

20 Claims, 4 Drawing Sheets

VOLTAMMETRIC MEASUREMENT OF HALIDE ION CONCENTRATION

CROSS-REFERENCE TO RELATED APPLICATIONS

This application is related to U.S. patent applications Ser. No. 09/968,202 (filed Oct. 1, 2001), now U.S. Pat. No. 6,572,753, Ser. No. 10/115,539 (filed Apr. 3, 2002) and Ser. No. 10/266,006 (filed Oct. 7, 2002) to Chalyt et al., which are assigned to the same assignee. The teachings of these patent applications are incorporated herein by reference.

BACKGROUND OF THE INVENTION

1. Field of the Invention

This invention is concerned with analysis of halide ions in solutions, and in particular with determination of the chloride concentration in acid copper electroplating baths, as a means of providing control over the deposit properties.

2. Description of the Related Art

Electroplating baths typically contain organic additives whose concentrations must be closely controlled in the low parts per million range in order to attain the desired deposit properties and morphology. One of the key functions of such additives is to level the deposit by suppressing the electrodeposition rate at protruding areas in the substrate surface and/or by accelerating the electrodeposition rate in recessed areas. Accelerated deposition may result from mass-transport-limited depletion of a suppressor additive species that is rapidly consumed in the electrodeposition process, or from accumulation of an accelerating species that is consumed with low efficiency. The most sensitive methods available for detecting leveling additives in plating baths involve electrochemical measurement of the metal electrodeposition rate under controlled hydrodynamic conditions, for which the additive concentration in the vicinity of the electrode surface is well-defined.

Cyclic voltammetric stripping (CVS) analysis [D. Tench and C. Ogden, J. Electrochem. Soc. 125, 194 (1978)] is the most widely used bath additive control method and involves cycling the potential of an inert electrode (e.g., Pt) in the plating bath between fixed potential limits so that metal is alternately plated on and stripped from the electrode surface. Such potential cycling is designed to establish a steady-state condition for the electrode surface so that reproducible results are obtained. Accumulation of organic films or other contaminants on the electrode surface can be avoided by periodically cycling the potential of the electrode in the plating solution without organic additives and, if necessary, polishing the electrode using a fine abrasive. Cyclic pulse voltammetric stripping (CPVS), also called cyclic step voltammetric stripping (CSVS), is a variation of the CVS method that employs discrete changes in potential during the analysis to condition the electrode so as to improve the measurement precision [D. Tench and J. White, J. Electrochem. Soc. 132, 831 (1985)]. A rotating disk electrode configuration is typically employed for both CVS and CPVS analysis to provide controlled hydrodynamic conditions.

For CVS and CPVS analyses, the metal deposition rate may be determined from the current or charge passed during metal electrodeposition but it is usually advantageous to measure the charge associated with anodic stripping of the metal from the electrode. A typical CVS/CPVS rate parameter is the stripping peak area ($A_r$) for a predetermined electrode rotation rate. The CVS method was first applied to control copper pyrophosphate baths (U.S. Pat. No. 4,132, 605 to Tench and Ogden) but has since been adapted for control of a variety of other plating systems, including the acid copper sulfate baths that are widely used by the electronics industry [e.g., R. Haak, C. Ogden and D. Tench, Plating Surf. Fin. 68(4), 52 (1981) and Plating Surf. Fin. 69(3), 62 (1982)].

Acid copper sulfate baths are employed in the "Damascene" process (e.g., P. C. Andricacos, Electrochem. Soc. Interface, Spring 1999, p.32; U.S. Pat. No. 4,789,648 to Chow et al.; U.S. Pat. No. 5,209,817 to Ahmad et al.) to electrodeposit copper within fine trenches and vias in dielectric material on semiconductor chips. In the Damascene process, as currently practiced, vias and trenches are etched in the chip's dielectric material, which is typically silicon dioxide, although materials with lower dielectric constants are under development. A barrier layer, e.g., titanium nitride (TiN), tantalum nitride (TaN) or tungsten nitride ($WN_x$), is deposited on the sidewalls and bottoms of the trenches and vias, typically by reactive sputtering, to prevent Cu migration into the dielectric material and degradation of the device performance. Over the barrier layer, a thin copper seed layer is deposited, typically by sputtering, to provide enhanced conductivity and good adhesion. Copper is then electrodeposited into the trenches and vias. Copper deposited on the outer surface, i.e., outside of the trenches and vias, is removed by chemical mechanical polishing (CMP). A capping or cladding layer (e.g., TiN, TaN or $WN_x$) is applied to the exposed copper circuitry to suppress oxidation and migration of the copper. Alternative barrier/capping layers based on electrolessly deposited cobalt and nickel are currently under investigation [e.g., A. Kohn, M. Eizenberg, Y. Shacham-Diamand and Y. Sverdlov, Mater. Sci. Eng. A302, 18 (2001)]. The "Dual Damascene" process involves deposition in both trenches and vias at the same time. In this document, the term "Damascene" also encompasses the "Dual Damascene" process.

Acid copper sulfate electroplating baths require a minimum of two types of organic additives to provide good leveling and satisfactory deposit properties. The "suppressor" additive (also called the "polymer", "carrier", or "wetter", depending on the bath supplier) is typically a polymeric organic species, e.g., high-molecular-weight polyethylene or polypropylene glycol, which adsorbs strongly on the copper cathode surface, in the presence of chloride ion, to form a film that sharply increases the overpotential for copper deposition. The "anti-suppressor" additive (also called the "brightener", "accelerator" or simply the "additive", depending on the bath supplier) counters the suppressive effect of the suppressor to provide the accelerated deposition needed for good leveling and bottom up filling of Damascene features. From the prior art literature [e.g., J. D. Reid and A. P. David, Plating Surf. Fin. 74(1), 66 (1987); J. J. Kelly, C. Tian and A. C. West, J. Electrochem. Soc. 146(7), 2540 (1999); and R. D. Mikkola and L. Chen, Proc. IEEE 2000 Int. Interconnect Tech. Conf., p. 117 (2000)], the presence of chloride ion is known to be essential to the functioning of the suppressor and anti-suppressor additives in acid copper baths. In order to avoid overplating ultrafine Damascene trenches and vias, a third additive called the "leveler" (or "booster", depending on the bath supplier) is used. The leveler is typically an organic compound containing nitrogen or oxygen that also tends to decrease the copper deposition rate. Plating bath suppliers generally provide additives in the form of solutions that may contain additives of more than one type, as well as other organic and inorganic addition agents. The suppressor additive may be comprised of more than one chemical species and generally involves a range of molecular weights.

In order to obtain satisfactory deposits, the concentrations of the organic additives used in acid copper plating baths must be accurately analyzed and controlled. The suppressor, anti-suppressor and leveler concentrations in acid copper sulfate baths can all be determined by CVS analysis methods based on the effects that these additives exert on the copper electrodeposition rate. At the additive concentrations typically employed, the effect of the suppressor in reducing the copper deposition rate is usually much stronger than that of the leveler so that the concentration of the suppressor can be determined by the usual CVS response curve or dilution titration analysis [W. O. Freitag, C. Ogden, D. Tench and J. White, Plating Surf. Fin. 70(10), 55 (1983)]. Likewise, the anti-suppressor concentration can be determined by the linear approximation technique (LAT) or modified linear approximation technique (MLAT) described by R. Gluzman [Proc. $70^{th}$ Am. Electroplaters Soc. Tech. Conf., Sur/Fin, Indianapolis, Ind. (June 1983)]. A method for measuring the leveler concentration in the presence of interference from both the suppressor and anti-suppressor is described in U.S. patent application Ser. No. 09/968,202 to Chalyt et al. (filed Oct. 1, 2001).

The concentration of chloride ion in acid copper plating baths must also be closely controlled (typically at a value in the 25 to 100 mg/L range) since chloride is essential to the functioning of the additive system. However, chloride ion specific electrodes are not suitable for use in acid copper plating baths because of the presence of interfering species (e.g., organic additives, copper ions and strong acid) that cause the electrode potential to drift with time. Another prior art method for chloride analysis involves titration with a solution of mercuric nitrate, which is a hazardous material that requires special handling and waste disposal. The calorimetric endpoint for this titration is also difficult to detect with sufficient accuracy, especially for an automated analysis system.

An alternative prior art method for chloride analysis of acid copper plating baths involves potentiometric titration with silver nitrate solution, for which the endpoint detection is readily automated and no hazardous waste is involved. However, the silver chloride precipitate produced during the titration is difficult to remove, and residues of the precipitate, or of a reducing agent (typically, sodium thiosulfate) used to dissolve it, can interfere with subsequent analyses performed in the same cell. The CVS methods used for analyses of organic additives in acid copper baths are particularly sensitive to interference from chloride and silver ions (derived from dissolution of the silver chloride precipitate) and reducing agents, which can affect the copper electrodeposition rate. Another disadvantage of this prior art method is that the silver nitrate solution is decomposed by ambient light and must be handled in darkened containers and tubing, which interfere with visual inspection of the reagent delivery system. In addition, this titration method is only moderately sensitive to chloride.

A sensitive and robust method for analysis of chloride in acid copper plating baths, without the use of contaminating or hazardous chemicals, would be useful for controlling industrial plating processes, particularly those employed by the electronics industry. Such a method would also be useful for other applications, for example, to monitor the quality of the feed water and effluents for industrial processes. A method for detecting other halides is also needed. Chloride ion is generally known to strongly affect the copper electrodeposition rate from acid copper plating baths containing organic additives [e.g., R. D. Mikkola and L. Chen, Proc. IEEE 2000 Int. Interconnect Tech. Conf., p. I1I7 (2000)] but the present inventors were the first to recognize that this effect might be used as a means of quantitative halide analysis.

SUMMARY OF THE INVENTION

This invention provides a method for determining the concentration of a halide ion (chloride, iodide or bromide) in an unknown solution from the effect that the halide ion exerts on the copper electrodeposition rate from a copper electrodeposition solution. In this method, a copper electrodeposition rate parameter is measured for the copper electrodeposition solution, a test solution, and a calibration solution. The copper electrodeposition solution includes copper ions, an anion (sulfate, for example), an acid (sulfuric acid, for example), and at least one organic additive at a predetermined concentration. Preferably, the copper electrodeposition solution contains substantially no halide ions, or contains a small predetermined concentration of a halide ion. The test solution comprises the copper electrodeposition solution and a known volume fraction of the unknown solution being analyzed. The calibration solution comprises the copper electrodeposition solution and a known concentration of the halide ion being analyzed, which may be added as a solution or a solid. The concentration of the halide in the unknown solution is determined by comparing the values of the electrodeposition rate parameter measured for the copper electrodeposition solution, the test solution, and the calibration solution. Preferably, a calibration curve is generated by measuring the electrodeposition rate parameter for a plurality of calibration solutions, and the halide concentration in the unknown solution is determined by interpolation of the rate parameter measured for the test solution with respect to the calibration curve. Alternatively, the halide concentration may be determined by the linear approximation method, for which the calibration solution comprises the test solution with a known concentration of the halide added.

The method of the present invention provides a sensitive measure of the halide concentration in the unknown solution since the effect of organic additives on the copper electrodeposition rate is generally small in the absence of halide ion but is large in the presence of halide ion. Consequently, halide derived from addition of the unknown solution to the copper electrodeposition solution (containing little or no halide ion) has a relatively large effect on the copper electrodeposition rate. Addition of halide to the copper electrodeposition solution may increase or decrease the copper electrodeposition rate, depending on the specific organic additives employed in the copper electrodeposition solution.

The method of the present invention is particularly useful for measuring the concentration of chloride ion in an acid copper sulfate electroplating bath. In a preferred embodiment, the copper electrodeposition solution contains the same organic additives as those used in the acid copper plating bath. In this case, addition of chloride ion to the copper electrodeposition solution typically produces a decrease in the copper electrodeposition rate, because of the dominant effect of the suppressor additive. The test solution comprises the copper electrodeposition solution and a known volume fraction of a sample of the copper plating bath. Organic additives present in the plating bath sample are diluted by addition of the plating bath sample to the copper electrodeposition solution so that their effect on the chloride analysis is generally small. A significantly different concentration (including zero concentration) of one or more of the additives may be utilized in the copper electrodeposition solution (compared to the copper plating bath) to improve the sensitivity, selectivity, and/or accuracy of the analysis.

The copper electrodeposition rate is preferably measured by the cyclic voltammetric stripping (CVS) method. A preferred electrodeposition rate parameter is the copper stripping peak area ($A_r$), which is preferably normalized by dividing the $A_r$ values for the test solution and the calibration solution by the $A_r(0)$ value for the copper electrodeposition solution. The normalized $A_r/A_r(0)$ parameter inherently provides a measure of the difference in the copper electrodeposition rate for a given test or calibration solution relative and that for the copper electrodeposition solution. Use of a normalized rate parameter also minimizes errors resulting from fluctuations in the temperature of the copper electrodeposition solution, and variations in the working electrode surface state. The halide concentration in the test solution is preferably determined by comparison of the $A_r/A_r(0)$ value for the test solution with a calibration plot of $A_r/A_r(0)$ vs. halide concentration (for a plurality of calibration solutions). The halide concentration in the unknown solution may then be calculated from the volume fraction of the unknown solution in the test solution.

The present invention provides a sensitive method for determining the concentration of chloride ions in acid copper plating baths without the use of extraneous reagents. Thus, the cross-contamination and waste disposal issues associated with the reagents and reaction products utilized in prior art methods are avoided. In addition, the method may be practiced using CVS instrumentation, which is widely used for analysis of organic additives in acid copper plating baths. This invention is useful for providing the close control of the chloride concentration in acid copper baths needed for optimum additive functioning and acceptable deposit properties. The method may also be used to measure the concentrations of other halides or halide mixtures that could be used in acid copper electroplating baths. The invention also provides a sensitive measure of the halide concentration in a wide variety of solutions, including drinking water and industrial process feed and effluent solutions.

Further features and advantages of the invention will be apparent to those skilled in the art from the following detailed description, taken together with the accompanying drawings.

DETAILED DESCRIPTION OF THE INVENTION

Figure 1:
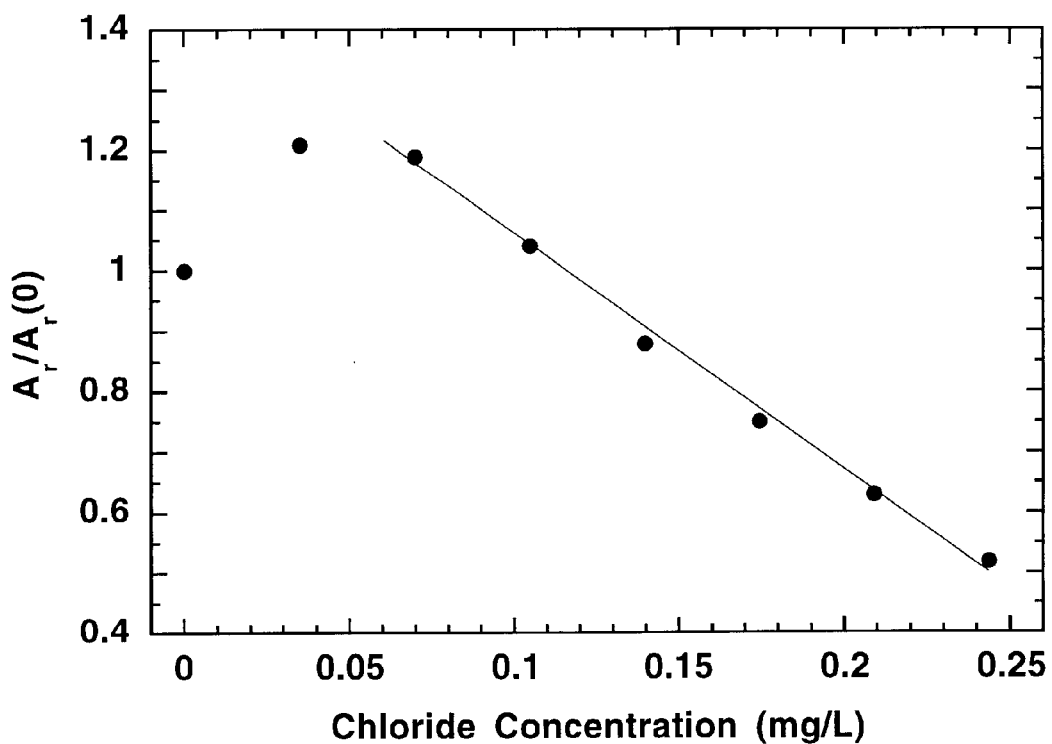
FIG. 1 shows a calibration plot of the CVS normalized copper stripping peak area, $A_r/A_r(0)$, as a function of the concentration of chloride ion added to an acid copper electrodeposition solution.

Technical terms used in this document are generally known to those skilled in the art. The term "electrode potential", or simply "potential", refers to the voltage occurring across a single electrode-electrolyte interface. In practice, the electrode potential often includes an appreciable resistive voltage drop in the electrolyte, which typically remains constant and does not affect voltammetric analysis results.

Voltammetric data may be generated by scanning the electrode potential at a constant rate or by stepping the potential, or by a combination of potential scanning and stepping. A "cyclic voltammogram" is a plot of current or current density (on the y-axis) versus the working electrode potential (on the x-axis) typically obtained by cycling the working electrode potential with time between fixed negative and positive limits. A "potentiostat" is an electronic device for controlling the potential of a working electrode by passing current between the working electrode and a counter electrode so as to drive the working electrode to a desired potential relative to a reference electrode. Use of a potentiostat avoids passing appreciable current through the reference electrode, which might change its potential. Operation in the three-electrode mode may also reduce errors in the electrode potential associated with the resistive voltage drop in the electrolyte.

As used in this document, the term "unknown solution" denotes a solution having an unknown concentration of halide to be determined by the analysis of the invention. The unknown solution may be a sample of a plating bath or of another solution. The term "plating bath" encompasses both electroplating baths and electroless plating baths, used to plate any metal. The copper electrodeposition rate used for the analysis of the invention is measured in a "copper electrodeposition solution" having predetermined concentrations of copper ions, an anion, an acid, and at least one organic additive. The plural term "copper ions" is used since copper is typically present in solution as $Cu^{2+}$ and $Cu^+$ species in various complexes with anions. In acid copper plating solutions, the $Cu^{2+}$ species is typically dominant but the $Cu^+$ species is formed as an intermediate during copper electrodeposition. The copper electrodeposition solution may also contain a small predetermined concentration of a halide ion. The symbol "$\underline{M}$" means molar concentration. The term "standard addition" generally means addition of a known volume of an unknown solution or of a standard halide solution to a known volume of a copper electrodeposition solution. The volume fraction is the volume of unknown solution or standard halide solution added to the copper electrodeposition solution divided by the total volume of the solution resulting from addition of the unknown solution or standard solution. The term "standard addition" also encompasses addition of a known weight of a solid halide salt to a known volume of a copper electrodeposition solution. Calibration data are typically handled as calibration curves or plots but such data may be tabulated and used directly, especially by a computer, and the terms "curve" or "plot" used in this document include tabulated data. As used in this document, the term "halide" encompasses chloride, bromide and iodide, but does not include fluoride, which is chemically atypical of the halides with respect to complexation and does not substantially enhance the effects of organic additives in acid copper plating baths.

The method of the present invention depends on the fact that organic additives used to brighten and level deposits from acid copper plating baths generally exert a strong effect on the copper electrodeposition rate only in the presence of halide ions. In a preferred embodiment, the copper electrodeposition rate is first measured in a copper electrodeposition solution containing predetermined concentrations of at least one organic additive and a small predetermined concentration of a halide ion (or no halide ion). The copper electrodeposition rate is then measured for a test solution comprised of the copper electrodeposition solution and a known volume fraction of an unknown solution. The change in the copper electrodeposition rate produced by such standard addition of the unknown solution to the copper electrodeposition solution provides a measure of the halide ion concentration in the unknown solution. A calibration curve is preferably generated by measuring the copper electrodeposition rate for the copper electrodeposition solution and for a plurality of calibration solutions comprised of the copper electrodeposition solution and known concentrations of the halide ion. In this case, the halide concentration in the unknown solution is determined by interpolation of the copper electrodeposition rate measured for the test solution with respect to the calibration curve. The analysis may be also be performed using only one calibration solution. For solutions containing more than one type of halide ion, the analysis yields the total concentration of halide ions.

Changes in the copper electrodeposition rate for the test and calibration solutions are preferably expressed as a normalized rate parameter. A preferred normalized rate parameter is the ratio of the copper electrodeposition rate for the test solution or calibration solution to that for the copper electrodeposition solution, which provides a measure of the copper deposition rate differential relative to the copper electrodeposition solution and minimizes errors associated with temperature fluctuations and changes in the working electrode surface state. Other normalized rate parameters may also be used, for example, the mathematical difference between the electrodeposition rate for the test solution or the calibration solution and that for the copper electrodeposition solution. The copper electrodeposition rate parameter may also be normalized as the ratio or difference of values measured under two well-defined hydrodynamic conditions, for example, at two electrode rotation rates (one of which may be zero).

A preferred copper electrodeposition solution for the analysis of the invention is an acid copper sulfate plating bath containing at least one organic additive and either a small predetermined concentration of halide ion or no added halide. Typical ranges for the major inorganic constituents of acid copper sulfate baths, which may be suitable ranges for the analysis of the present invention, are 40–240 g/L copper sulfate pentahydrate and 1–240 g/L sulfuric acid. The copper electrodeposition solution preferably contains a suppressor additive (polyethylene glycol or polypropylene glycol, for example), and may contain an anti-suppressor additive [bis-(3-sulfopropyl) disulfide or 3-mercapto-1-propanosulfonate, for example] and/or a leveler additive (benzotriazole, for example). The various additives are usually obtained from bath suppliers in the form of solutions for which the actual additive species and their concentrations may not be known. The concentrations of such additive solutions recommended by the bath supplier are generally suitable for use in the copper electrodeposition solution of the present invention. The copper electrodeposition solution may employ a variety of anions, including sulfate, alkylsulfonate, sulfamate, fluoroborate, citrate, and mixtures thereof.

The suppressor additive used in the copper electrodeposition solution typically comprises a polymeric species having a range of molecular weights. For the polyethylene glycol suppressor, the average molecular weight is preferably between 500 and 15,000, but higher or lower average molecular weights may be used. Polyethylene glycol concentrations from 0.1 to 1.0 g/L are preferred but other concentrations may be used.

For analysis of the chloride ion concentration in acid copper electroplating baths, a preferred copper electrodeposition solution contains either a predetermined small concentration of chloride (0.1 mg/L, for example) or substantially no chloride, but otherwise includes the same concentrations of inorganic constituents as the plating bath being analyzed. For acid copper sulfate plating baths, the inorganic constituents are typically copper ions, sulfate and sulfuric acid, but other metal ions (e.g., tin ions) and other anions (e.g., citrate) may also be included in the bath. The concentrations of the inorganic constituents of the copper electrodeposition solution are preferable the same as those of the plating bath, which minimizes the effects of these constituents on the analysis. However, a wide range of acid copper compositions may be used.

A preferred copper electrodeposition solution for analysis of chloride ion in copper plating baths also contains the same organic additive species as the plating bath being analyzed. These include a suppressor additive, an anti-suppressor additive, and, in some cases, a leveler additive, which are typically supplied as solutions that may contain more than one chemical species. The concentrations of the various additives in the copper electrodeposition solution may differ from those in the plating bath. For example, an excess of suppressor additive may be used in the copper electrodeposition solution to ensure that the effect of the suppressor additive, which depends strongly on the chloride concentration, is dominant. Since the effect of each of the additives generally depends on the chloride concentration, a copper electrodeposition solution containing only one additive species (a suppressor, for example) may be used for the analysis. For copper electrodeposition solutions in which the anti-suppressor effect is dominant, the copper electrodeposition rate increases with increased chloride concentration.

For the method of the present invention, the copper electrodeposition rate is preferably determined by cyclic voltammetric stripping (CVS) or cyclic pulse voltammetric stripping (CPVS). The latter is also called cyclic step voltammetric stripping (CSVS). As used in this document, the term "cyclic voltammetric stripping" or "CVS" implicitly includes the CPVS method, which is a variation of the CVS method. Likewise, the term "CVS rate parameter" includes the analogous CPVS rate parameters.

In the CVS method, the potential of an inert working electrode, typically platinum, is cycled in a copper electrodeposition solution at a constant rate between fixed potential limits so that copper is alternately electrodeposited on the electrode surface and anodically stripped back into the solution. Preferably, a rotating disk electrode configuration is used for the working electrode to control solution mass transport so as to improve the sensitivity and reproducibility of the analysis results. The copper deposition rate is preferably measured via the copper stripping peak area at a constant electrode rotation rate ($A_r$) but may also be determined from the stripping peak height, or from the electrode impedance, current (including average current), or integrated current (charge) measured for a predetermined cathodic potential or potential range (with or without electrode rotation). All of these rate parameters provide a relative measure of the copper electrodeposition rate that can readily be used for comparisons only when the measurement conditions are the same.

Preferably, the $A_r$ values measured for the test and calibration solutions are divided by the $A_r(0)$ value for the copper electrodeposition solution. The normalized $A_r/A_r(0)$ parameter provides a measure of the difference in copper electrodeposition rate for the test and calibration solutions relative to that for the copper electrodeposition solution. Use of a normalized rate parameter also minimizes errors resulting from fluctuations in the solution temperature and variations in the working electrode surface state. In this case, the halide ion concentration in a test solution is preferably determined by comparison of the $A_r/A_r(0)$ value for the test solution with a calibration plot of $A_r/A_r(0)$ vs. halide ion concentration (for a plurality of calibration solutions). The halide concentration in the unknown solution may then be calculated from the volume fraction of unknown solution in the test solution. The electrodeposition rate parameter for the test and calibration solutions may also be normalized by other procedures, for example, via the mathematical difference with respect to the electrodeposition rate parameter measured for the copper electrodeposition solution, or via the ratio or difference for electrodeposition rates measured at two electrode rotation rates.

A preferred approach is to perform a CVS dilution titration by measuring $A_r(0)$ for the copper electrodeposition solution, and then measuring $A_r$ after each of a plurality of standard additions of the unknown solution to the copper electrodeposition solution. The halide concentration in the unknown solution is determined from the volume fraction of unknown solution added to the copper electrodeposition solution at the endpoint for the dilution titration, which is a predetermined $A_r/A_r(0)$ value (0.30, for example). This approach ensures that the copper electrodeposition rate differentials inherent in the $A_r/A_r(0)$ values is sufficiently large to provide reproducible results, and permits several data points to be averaged to further improve the precision of the analysis results.

For CVS electrodeposition rate measurements, a plurality of potential cycles is typically employed to condition the working electrode surface so as to provide reproducible results. Electrode conditioning may be performed for a predetermined number of cycles (3 cycles, for example), or until a steady-state electrode condition is indicated by substantially equivalent voltammograms or voltammetric features on successive cycles. Typically, steady state is indicated by successive $A_r$ values that differ by less than a predetermined percentage (0.5%, for example).

The inert working electrode for CVS measurements may be comprised of any suitable electrically conducting material that is stable in the background electrolyte under the conditions used for the voltammetric analysis but is preferably comprised of a noble metal, for example, platinum, iridium, gold, osmium, palladium, rhenium, rhodium, ruthenium, and alloys thereof. Other oxidation-resistant metals and alloys, stainless steel, for example, may also be used as working electrode materials. A typical CVS rotating disk electrode is comprised of a platinum metal disk (3–5 mm diameter), with an electrical contact wire on the backside, embedded flush with one end of an insulating plastic cylinder (10–20 mm diameter). The rotating disk electrode may be fabricated by press fitting the metal disk into a hole in the plastic but is preferably fabricated by hot pressing, which forms a seal between the metal and the plastic that prevents intrusion of the solution. A suitable plastic for mounting rotating disk electrodes by hot pressing is polytrifluorochloroethylene (Kel-F®). The rotating disk electrode is usually rotated at a constant rate (100–5000 rpm) but the electrode rotation may be modulated with time.

Precise control over the working electrode potential needed for CVS measurements is typically provided via an electronic potentiostat in conjunction with a counter electrode and a reference electrode, e.g., silver-silver chloride (SSCE), mercury-mercury sulfate, or saturated calomel electrode (SCE). A double junction may be used to extend the life of the reference electrode by inhibiting intrusion of plating bath species. The counter electrode may be comprised of an inert metal or copper. Depolarizers (sulfur or phosphorus, for example) may be included in a copper counter electrode to facilitate copper dissolution so as to avoid breakdown of the copper electrodeposition solution. Practically any electrical conductor that resists oxidation and reduction in the copper electrodeposition solution may be used as an inert counter electrode, including metals, alloys and conducting oxides (mixed titanium-ruthenium oxide, for example). A preferred inert counter electrode material is 316 stainless steel, which is highly oxidation-resistant and relatively inexpensive, but other types of stainless steel or other oxidation-resistant alloys (Inconel, for example) may also be used. Other suitable inert counter electrode materials include noble metals, for example, platinum, iridium, gold, osmium, palladium, rhenium, rhodium, ruthenium, and alloys thereof.

Metal electrodeposition rates according to the present invention may also be measured by methods other than CVS, including those based on measurements of the ac impedance of the cathode, for example. The same electrode materials and configurations may be used for such alternative methods. Although the precision and reproducibility of the analysis might be degraded, current measurements reflecting the metal electrodeposition rate could also be made at a stationary electrode and/or without potential cycling. If a stationary working electrode is used for the halide ion analysis of the present invention, the hydrodynamic conditions at the electrode is surface are preferably controlled, by stirring or pumping the solution, for example.

Improved results for the analysis of the present invention may be provided by optimizing the CVS measurement parameters. The key CVS measurement parameters and their typical ranges for acid copper systems include the electrode rotation rate (100–10,000 rpm), potential scan rate (10–1000 mV/s), negative potential limit (−0.05 to −0.5 V vs. SSCE) and positive potential limit (1.4 to 1.8 V vs. SSCE). A positive potential limit of relatively high voltage (in the oxygen evolution region) is typically used so that contaminants adsorbed on the electrode surface are removed by electrochemical oxidation on each cycle, which provides more reproducible results. Additional CPVS measurement parameters include the potentials and hold times for the pulses or steps used. The accuracy of the electrodeposition rate measurement may be improved by employing a slightly elevated solution temperature (typically, 3° or 4° C. above room temperature), which can be more consistently maintained.

Within the scope of the present invention, variations in the analysis procedures and data handling will be apparent to those skilled in the art. For example, the halide concentration may be determined by linear approximation analysis. In this case, a copper electrodeposition rate parameter (e.g., $A_r$) is measured for the copper electrodeposition solution before and after addition of a known volume fraction of an unknown solution. The electrodeposition rate parameter measurement is then repeated in this test solution after one or more standard additions of halide ion. The concentration of the halide in the unknown solution is calculated assuming that the electrodeposition rate parameter varies linearly with halide concentration, which is verified if the changes in the rate parameter produced by standard additions of the same amount of halide ion are equivalent. In this case, standard addition of halide ion to the test solution yields a calibration solution so that a separate calibration curve is not needed. An analogous procedure may be used when the variation in the electrodeposition rate parameter with halide concentration is non-linear but is nonetheless mathematically predictable.

The invention is particularly useful for analysis of chloride ion in acid copper sulfate electroplating baths. However, the method of the invention may also be applied to analysis of other halide ions (bromide and iodide), which are chemically similar and might be used instead of chloride, or in combination with chloride, in acid copper plating baths. For baths employing mixed halides, the analysis would yield a total halide concentration or an effective halide concentration. The invention may also be applied to analysis of halides in acid copper sulfate baths containing additional anions (citrate, for example), or acid copper baths based on alternative anions (alkylsulfonate, sulfamate, fluoroborate and citrate, for example). The invention may also be applied to analysis of halides in baths used to electrodeposit copper alloys (copper-tin alloys, for example) or other metals (nickel, gold, tin and lead, for example).

In addition, the method of the present invention may be applied to measure the halide concentration in a wide variety of unknown solutions, including drinking water and industrial process feed and effluent solutions. It is often necessary to monitor halides in process feed solutions to avoid unwanted side reactions, such as corrosion reactions. Halide in effluent solutions are often monitored for compliance with environmental regulations.

DESCRIPTION OF A PREFERRED EMBODIMENT

In a preferred embodiment of the present invention, the concentration of halide ion in an unknown solution is determined from the effect of standard addition of the unknown solution on the CVS stripping peak area ($A_r$) measured at a rotating Pt disk electrode in a copper electrodeposition solution. Preferably, the copper electrodeposition solution contains a small predetermined concentration of halide (0.1 mg/L chloride, for example) or substantially no halide. For analysis of halide in an acid copper plating bath, the concentrations of other bath constituents are preferably maintained within the ranges recommended by the bath supplier. After each standard addition, sufficient time should be allowed for stirring via the rotating disk electrode (or other means) to provide a homogeneous solution. During measurements, the solution temperature should be maintained at a constant value (within ±0.5° C.) around room temperature.

For $A_r$ measurements, the electrode potential is preferably cycled at a constant rate between fixed positive and negative limits. Typical ranges for the other CVS measurement parameters are 100–5000 rpm for the electrode rotation rate, 50–500 mV/s for the potential scan rate, and 1.4 to 1.8 V vs. SSCE for the positive potential limit. The potential of the rotating disk electrode is preferably controlled relative to a reference electrode via a potentiostat and a counter electrode.

Prior to the halide analysis, the potential of the working electrode is preferably cycled (over the potential range used for the analysis) in the copper electrodeposition solution to condition the electrode surface. For both the electrode conditioning and the halide analysis, the potential of the working electrode is preferably cycled for a predetermined number of cycles, typically three. Alternatively, the potential of the working electrode is cycled until successive $A_r$ values differ by less than a predetermined percentage (typically 0.5%).

The efficacy of the present invention was demonstrated via CVS measurements of $A_r$ at a platinum disk electrode (4 mm diameter) rotating at 2500 rpm in a copper electrodeposition solution (without halide added), calibration solutions (containing chloride, bromide or iodide), and various test solutions. Solutions were prepared using de-ionized water. The copper electrodeposition solution contained 75 g/L copper sulfate pentahydrate, 100 mL/L concentrated sulfuric acid, 1.0 mL/L Viaform Accelerator additive, 5.0 mL/L Viaform Suppressor additive, and 10 mL/L Viaform Leveler additive. Calibration solutions were prepared by standard addition of 50 mg/L halide solutions to 100 mL of the copper electrodeposition solution. For chloride dilution titration tests, copper plating bath samples containing known chloride concentrations (30–70 mg/L) were added to 50 mL of the copper electrodeposition solution. Measurements were also made for both the low acid and high acid formulations of the Viaform acid copper sulfate plating bath (Enthone OMI Corp.), and for a proprietary acid copper sulfate plating bath (not sold commercially).

CVS measurements were made under potentiostatic control using a Qualilab QL-10 plating bath analyzer or QLCA-320 Online Chemical Measurement System (ECI Technology, Inc.). The counter electrode was a stainless steel rod and the reference electrode was a modified silver-silver chloride electrode (SSCE-M) for which the solution in a standard SSCE electrode was replaced with a saturated AgCl solution also containing 0.1 $\underline{M}$ KCl and 10 volume % sulfuric acid. The working electrode potential was scanned at 200 mV/s between a positive limit of ±1.575 V and a negative limit of –0.225 V vs. SSCE-M. For $A_r$ and $A_r(0)$ measurements, the anodic current was integrated from the zero-current potential (at the cathodic-anodic crossover) to 0.30 V vs. SSCE-M. The electrode was conditioned for two potential cycles; $A_r$ or $A_r(0)$ was recorded for the third cycle. During CVS measurements, the solution temperature was controlled at 25° C. within ±0.5° C.

FIG. 1 shows a calibration plot of the CVS normalized rate parameter $A_r/A_r(0)$ as a function of the chloride ion concentration in the copper electrodeposition solution. The value of $A_r/A_r(0)$ is seen to decrease linearly with chloride concentration above about 0.05 mg/L (ppm). High sensitivity of $A_r/A_r(0)$ to the chloride concentration in the linear region is evident. A linear response to chloride ion may be provided in practice via addition of about 0.05 mg/L chloride to the copper electrodeposition solution.

Figure 2:
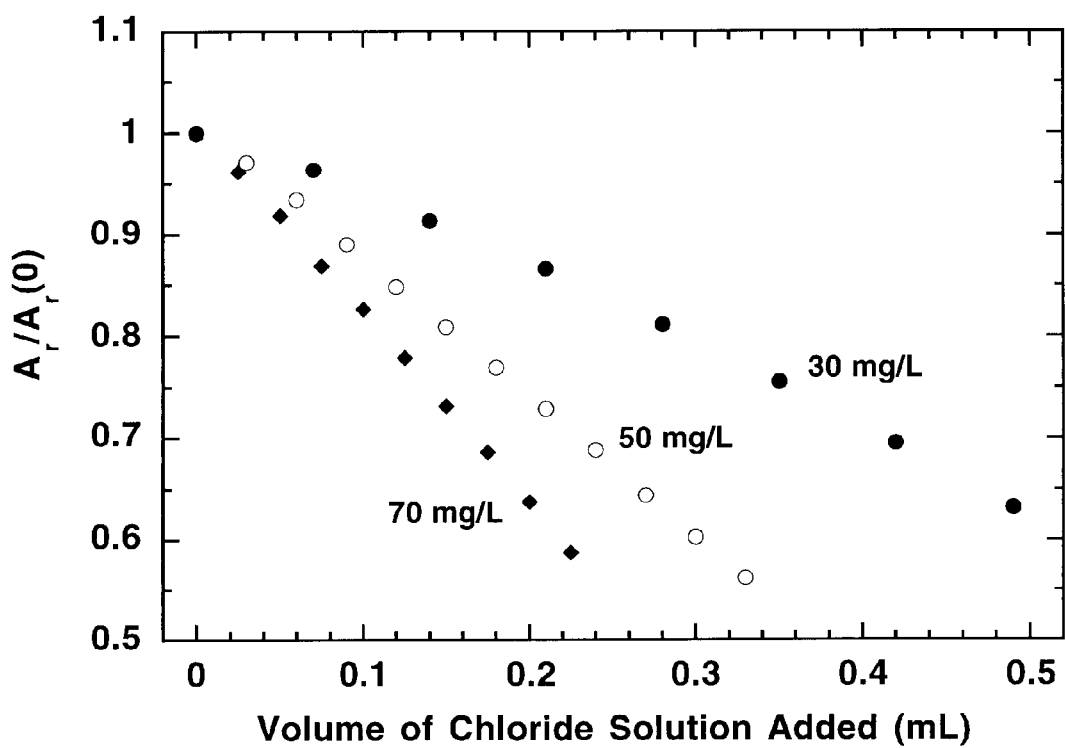
FIG. 2 shows dilution titration plots of $A_r/A_r(0)$ vs. Volume fractions of plating bath samples (containing 30, 50 or 70 mg/L chloride ion) added to 50 mL of the copper electrodeposition solution (of FIG. 1).

FIG. 2 shows dilution titration plots of $A_r/A_r(0)$ vs. volume fraction of plating bath samples (containing various concentrations of chloride ion) added to 50 mL of the copper electrodeposition solution. The plating bath was the Viaform high acid formulation and contained 75 g/L copper sulfate pentahydrate, 100 mL/L concentrated sulfuric acid, 2.0 mL/L Viaform Accelerator, 8.0 mL/L Viaform Suppressor, 1.5 mL/L Viaform Leveler, and 30, 50 or 70 mg/L chloride ion. These chloride concentrations are representative of those typically found in acid copper plating baths. In all cases, the value of $A_r/A_r(0)$ decreased linearly with the volume fraction of the plating bath sample added, and the volume fraction for a given $A_r/A_r(0)$ value exhibited a strong dependence on the chloride concentration in the plating bath sample.

Figure 3:
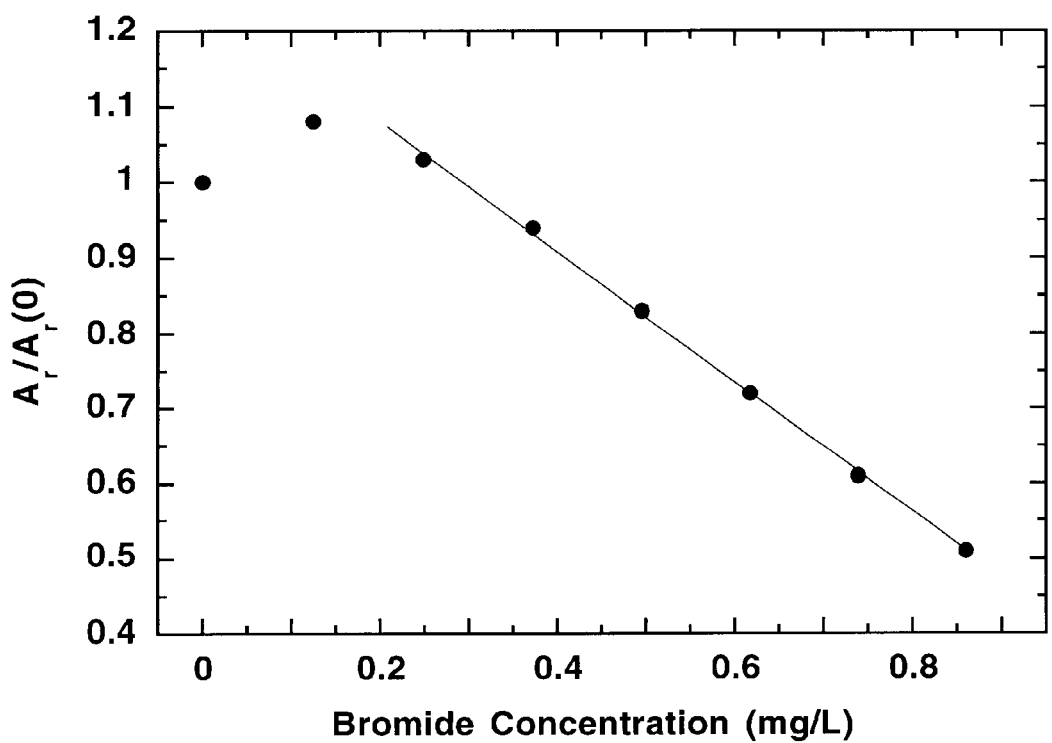
FIG. 3 shows a calibration plot of the CVS normalized copper stripping peak area, $A_r/A_r(0)$, as a function of the concentration of bromide ion added to the acid copper electrodeposition solution (of FIG. 1).

FIG. 3 shows a calibration plot of the CVS normalized rate parameter $A_r/A_r(0)$ as a function of the bromide ion concentration in the copper electrodeposition solution. The value of $A_r/A_r(0)$ is seen to decrease linearly with bromide concentration above about 0.2 mg/L (ppm). High sensitivity of $A_r/A_r(0)$ to the bromide concentration in the linear region is evident. A linear response to bromide ion may be provided in practice via addition of about 0.2 mg/L bromide to the copper electrodeposition solution.

Figure 4:
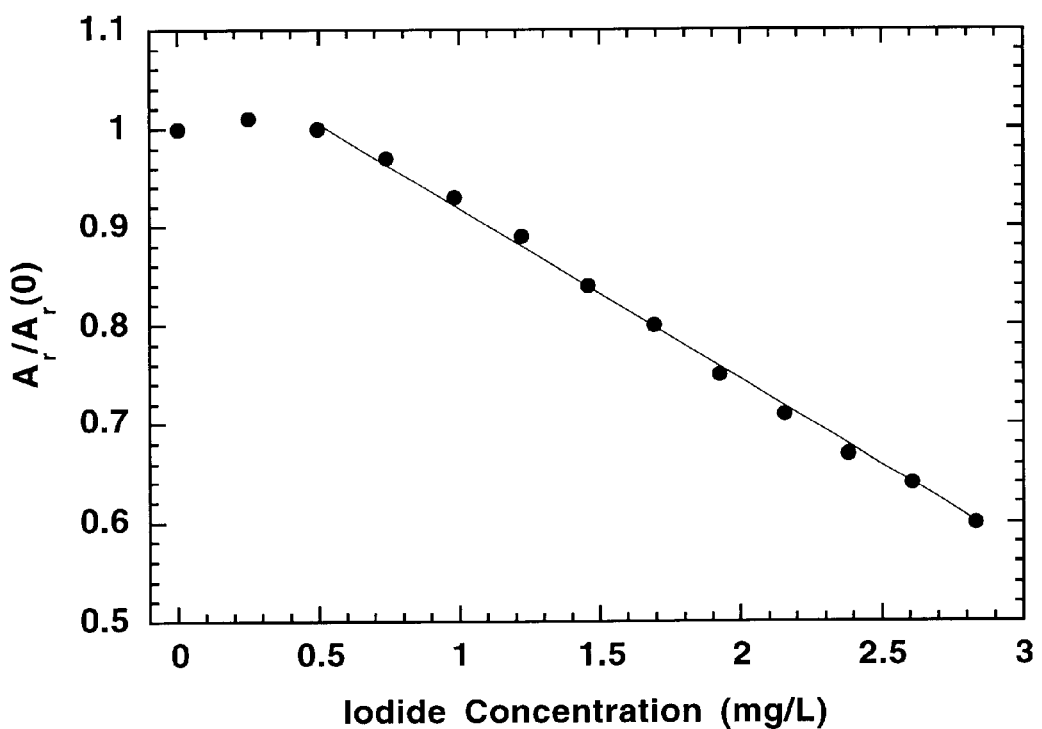
FIG. 4 shows a calibration plot of the CVS normalized copper stripping peak area, $A_r/A_r(0)$, as a function of the concentration of iodide ion added to the acid copper electrodeposition solution (of FIG. 1).

FIG. 4 shows a calibration plot of the CVS normalized rate parameter $A_r/A_r(0)$ as a function of the iodide ion concentration in the copper electrodeposition solution. The value of $A_r/A_r(0)$ is seen to decrease linearly with iodide concentration above about 0.5 mg/L (ppm). High sensitivity of $A_r/A_r(0)$ to the iodide concentration in the linear region is evident. A linear response to iodide ion may be provided in practice via addition of about 0.5 mg/L iodide to the copper electrodeposition solution.

EXAMPLE 1

The method of the present invention was used to analyze the chloride concentration in high-acid Viaform acid copper plating baths having concentrations of the various constituents that corresponded to the target values, and the high and low supplier specification limits. The low-specification bath contained 58 g/L copper sulfate pentahydrate, 100 mL/L concentrated sulfuric acid, 30 mg/L chloride ion, 1.0 mL/L Viaform Accelerator, 4.0 mL/L Viaform Suppressor, and 1.0 mL/L Viaform Leveler. The target-specification bath contained 75 g/L copper sulfate pentahydrate, 100 mL/L concentrated sulfuric acid, 50 mg/L chloride ion, 2.0 mL/L Viaform Accelerator, 8.0 mL/L Viaform Suppressor, and 1.5 mL/L Viaform Leveler. The high-specification bath contained 90 g/L copper sulfate pentahydrate, 100 mL/L concentrated sulfuric acid, 70 mg/L chloride ion, 3.0 mL/L Viaform Accelerator, 12.0 mL/L Viaform Suppressor, and 2.0 mL/L Viaform Leveler. Chloride analyses were performed via dilution titration to 0.75 for the $A_r/A_r(0)$ value. Table 1 shows that the chloride analysis values agreed well with those expected from the make-up solution composition.

TABLE 1

Chloride Analysis Results for
Viaform Acid Copper Plating Baths

| Bath Composition | Expected (mg/L) | Analysis (mg/L) | Error (%) |
|---|---|---|---|
| Low-Specification | 30 | 31.1 | 3.5 |
| Low-Specification | 30 | 30.5 | 1.6 |
| Target | 50 | 51.6 | 3.3 |
| Target | 50 | 50.3 | 0.6 |
| High-Specification | 70 | 71.2 | 1.8 |

EXAMPLE 2

The method of the present invention was used to analyze the chloride concentration in low-acid Viaform acid copper plating baths having concentrations of the various constituents that corresponded to the target values, and the high and low supplier specification limits. Eighteen chloride measurements were made over a one week period. The low-specification bath contained 140 g/L copper sulfate pentahydrate, 8.0 g/L sulfuric acid, 40 mg/L chloride ion, 4.0 mL/L Viaform Accelerator, 1.5 mL/L Viaform Suppressor, and 0.5 mL/L Viaform Leveler. The target-specification bath contained 160 g/L copper sulfate pentahydrate, 10.0 g/L sulfuric acid, 50 mg/L chloride ion, 6.0 mL/L Viaform Accelerator, 2.0 mL/L Viaform Suppressor, and 1.0 mL/L Viaform Leveler. The high-specification bath contained 180 g/L copper sulfate pentahydrate, 12.0 g/L sulfuric acid, 60 mg/L chloride ion, 8.0 mL/L Viaform Accelerator, 2.5 mL/L Viaform Suppressor, and 1.5 mL/L Viaform Leveler. Chloride analyses were performed via dilution titration to 0.75 for the $A_r/A_r(0)$ value. For the low-specification (40 mg/l chloride), target (50 mg/L chloride), and high-specification (60 mg/L chloride) baths, respectively, the average chloride analysis results and the relative standard deviation (in parentheses) for 18 measurements were 40.17 mg/L (1.50%), 50.17 mg/L (1.41%) and 60.04 mg/L (1.37%).

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for determining the concentration of a halide ion in an unknown solution, comprising the steps of:

measuring a copper electrodeposition rate parameter for a copper electrodeposition solution comprising copper ions, an anion, an acid, and at least one organic additive selected from the group consisting of suppressor, anti-suppressor and leveler;

measuring the copper electrodeposition rate parameter for a test solution comprising the copper electrodeposition solution and a known volume fraction of the unknown solution;

measuring the copper electrodeposition rate parameter for at least one calibration solution comprising the copper electrodeposition solution and a known concentration of the halide ion; and comparing the copper electrodeposition rate parameters measured, in said steps of measuring, for the copper electrodeposition solution, the test solution, and the calibration solution to determine the concentration of the halide ion in the unknown solution.

2. The method of claim 1, wherein the halide ion is selected from the group consisting of chloride, bromide, iodide, and mixtures thereof.

3. The method of claim 1, wherein the unknown solution is an acid copper electroplating bath.

4. The method of claim 1, wherein the anion is selected from the group consisting of sulfate, alkylsulfonate, sulfamate, fluoroborate, citrate, and mixtures thereof.

5. The method of claim 1, wherein the electrodeposition rate parameter is measured by a method selected from the group consisting of CVS and CPVS.

6. The method of claim 5, wherein the electrodeposition rate parameter is selected from the group consisting of stripping peak area, stripping peak height, current at a predetermined cathodic potential, integrated current over a predetermined cathodic potential range, and average current over a predetermined cathodic potential range.

7. The method of claim 1, wherein the electrodeposition rate parameter is measured by an alternating current (ac) method.

8. The method of claim 1, wherein the electrodeposition rate parameters measured, in said steps of measuring, for the test solution and the calibration solution are normalized relative to the electrodeposition rate parameter measured for the copper electrodeposition solution.

9. The method of claim 1, wherein the calibration solution further comprises a known volume fraction of the unknown solution.

10. A method for determining the concentration of chloride ion in an acid copper electroplating bath, comprising the steps of:
   measuring a copper electrodeposition rate parameter for a copper electrodeposition solution comprising copper ions, an anion, an acid, and at least one organic additive selected from the group consisting of suppressor, anti-suppressor and leveler;
   measuring the copper electrodeposition rate parameter for a test solution comprising the copper electrodeposition solution and a known volume fraction of the acid copper electroplating bath;
   measuring the copper electrodeposition rate parameter for at least one calibration solution comprising the copper electrodeposition solution and a known concentration of chloride ion; and
   comparing the copper electrodeposition rate parameters measured, in said steps of measuring, for the copper electrodeposition solution, the test solution, and the calibration solution to determine the concentration of chloride ion in the acid copper electroplating bath.

11. The method of claim 10, wherein the anion is selected from the group consisting of sulfate, alkylsulfonate, sulfamate, fluoroborate, citrate, and mixtures thereof.

12. The method of claim 10, wherein the acid copper electroplating bath includes an anion selected from the group consisting of alkylsulfonate, sulfamate, fluoroborate, citrate, and mixtures thereof.

13. The method of claim 10, wherein the electrodeposition rate parameter is measured by a method selected from the group consisting of CVS and CPVS.

14. The method of claim 13, wherein the electrodeposition rate parameter is selected from the group consisting of stripping peak area, stripping peak height, current at a predetermined cathodic potential, integrated current over a predetermined cathodic potential range, and average current over a predetermined cathodic potential range.

15. The method of claim 10, wherein the electrodeposition rate parameter is measured by an alternating current (ac) method.

16. The method of claim 10, wherein the electrodeposition rate parameters measured, in said steps of measuring, for the test solution and the calibration solution are normalized relative to the electrodeposition rate parameter measured for the copper electrodeposition solution.

17. The method of claim 10, wherein the calibration solution further comprises a known volume fraction of the acid copper electroplating bath.

18. A method for determining the concentration of chloride ion in an acid copper sulfate electroplating bath, comprising the steps of:
   measuring a CVS copper stripping peak area for a copper electrodeposition solution comprising copper ions, sulfate ion, sulfuric acid, and at least one organic additive selected from the group consisting of suppressor, anti-suppressor and leveler;
   measuring the CVS copper stripping peak area for a test solution comprising the copper electrodeposition solution and a known volume fraction of the acid copper sulfate electroplating bath;
   measuring the CVS copper stripping peak area for at least one calibration solution comprising the copper electrodeposition solution and a known concentration of chloride ion; and
   comparing the CVS copper stripping peak areas measured, in said steps of measuring, for the copper electrodeposition solution, the test solution, and the calibration solution to determine the concentration of chloride ion in the acid copper sulfate electroplating bath.

19. The method of claim 18, wherein the CVS stripping peak areas measured, in said steps of measuring, for the test solution and the calibration solution are normalized relative to the CVS stripping peak area measured for the copper electrodeposition solution.

20. The method of claim 18, wherein the calibration solution further comprises a known volume fraction of the acid copper sulfate electroplating bath.

* * * * *